United States Patent [19]

Mulvey et al.

[11] Patent Number: 4,529,584
[45] Date of Patent: Jul. 16, 1985

[54] DENTIFRICE COMPOSITION

[75] Inventors: Patricia S. Mulvey, Manalapan, N.J.; Harry Hayes, Warrington, England; Richard J. Crawford, Asbury, N.J.

[73] Assignee: Colgate-Palmolive Company, New York, N.Y.

[21] Appl. No.: 564,966

[22] Filed: Dec. 23, 1983

[51] Int. Cl.$^3$ .......................... A61K 7/16; A61K 7/18
[52] U.S. Cl. ......................................... 424/52; 424/49
[58] Field of Search ...................... 222/192; 424/49-58

[56] References Cited

U.S. PATENT DOCUMENTS

| | | | |
|---|---|---|---|
| 3,828,977 | 8/1974 | Borchert | 222/95 |
| 3,838,796 | 10/1974 | Cohen | 222/105 |
| 3,932,606 | 1/1976 | Barth et al. | 424/52 |
| 3,939,261 | 2/1976 | Barth | 424/52 X |
| 4,029,760 | 6/1977 | De Roeck et al. | 324/48 |
| 4,171,757 | 10/1979 | Diamond | 222/389 |
| 4,353,890 | 10/1982 | Scott | 424/49 |
| 4,444,747 | 4/1984 | Hayes et al. | 424/52 |
| 4,457,908 | 7/1984 | Scott | 424/49 |
| 4,482,536 | 11/1984 | Hayes et al. | 424/52 |

FOREIGN PATENT DOCUMENTS 56-115711  9/1981  Japan .
2070695  10/1981  United Kingdom .

OTHER PUBLICATIONS

Genu Product Description-Genuvisco Type 0819.
FMC Bulletin-Viscarin TP-5.
Colgate's New Pump Dispenser: MFP Fluoride Gel (U.S. Pat. No. 3,911,102).

*Primary Examiner*—Shep K. Rose
*Attorney, Agent, or Firm*—Robert L. Stone; Murray M. Grill; Herbert S. Sylvester

[57] ABSTRACT

A dentifrice composition of desirable rheological properties suitable for efficient filling into a mechanically operated or pressure differential dentifrice dispenser and extrusion therefrom which dentifrice comprises an alpha-alumina trihydrate polishing agent and many active ingredients and a gelling agent mixture of a cellulosic gelling agent such as sodium carboxymethyl cellulose and iota-carrageenan.

5 Claims, No Drawings

DENTIFRICE COMPOSITION

This invention relates to a dentifrice composition. In particular, it relates to a dentifrice composition having desirable rheological properties suitable for efficient filling into a mechanically operated or pressure differential dentifrice dispenser and extrusion therefrom.

A dentifrice is generally recognisable by its creamy or gel consistency and may commonly be called a dental cream, a toothpaste or, in some cases, a clear gel or opacified gel toothpaste. Indeed, it can be characterised as a semi-solid, for instance, being essentially solid when standing on the bristles of a toothbrush and essentially liquid such as during manufacture with agitation and filling into a container or when subject to pressure to extrude the dentifrice from its container.

The creamy consistency of dentifrices is typically imparted by a gelling or binding agent. In the past, gelling agents have been selected primarily to provide ease of dispersion of the dentifrice in the oral cavity. Many gelling agents such as cellulosic materials, seaweed derivatives, gums and clays meet this criteria. However, some gelling agents while generally desirable for dentifrices packaged in flexible tubes, do cause disadvantages when the dentifrices are packaged in mechanically operated or pressure differential dispensers.

Dentifrices containing conventional polishing agents such as alpha-alumina trihydrate and conventional gelling agents such as sodium carboxymethyl cellulose or hydroxyethyl cellulose or mixtures thereof can be desirably filled into flexible tubes or mechanically operated or pressure differential dispensers and extruded therefrom. However, when the dentifrice contains many active ingredients difficulties may occur when attempting to fill a dentifrice into a mechanically operated or pressure differential dispenser and/or when attempting to extrude it therefrom. In particular, leakage from orifices in the dispensers may occur during filling or shipping and the product can be difficult to extrude in rheologically desirable ribbon form.

Dentifrices which are thick or tend to thicken may become increasingly difficult for a consumer to extrude from a dentifrice tube over a period of time. In other words, the consumer may have to increase pressure on a dentifrice tube containing such a dentifrice during the period of use in order to soften or liquify the semi-solid dentifrice mass to extrude it. This has not been a major problem in the past since formulations can be adjusted to use less gelling agent to strike a balance at not being too soft at the start of use and too thick at the end and in any event consumers have readily adjusted to applying the amount of pressure necessary to extrude the desired amount of dentifrice on to bristles of a toothbrush.

Dentifrices which are thin upon extrusion from a tube have also been tolerated during use if they set to more solid form on toothbrush bristles within a few seconds. Thus, the type of gelling agent could be widely varied for dentifrices packaged in tubes. Indeed, the Copenhagen Pectin Factory Ltd of Little Skensved, Denmark, a subsidiary of Hercules Inc of Wilmington Del., USA has proposed its product Genuvisco Type 0819, an iota-carrageenan (i-carrageenan), as a possible thickener for toothpaste. I-carrageenan available from Marine Colloids Division of FMC Corp of Springfield, N.J., as Viscarin TP-5 has also been proposed for possible toothpaste with toothpaste containing dicalcium phosphate or silica. Moreover, i-carrageenan has been disclosed as a thickener component together with k-carrageenan and alkali metal alginate for a dentifrice containing galactan galactose in Japanese Patent Publication No. 56 115711, published Sept. 11, 1981, of Lion Dentifrice Ltd. Xanthan in another type of gelling agent which can be used to provide a dentifrice which does not unduly thicken.

When a dentifrice dispenser which operates mechanically or by pressure differential is employed, conventional techniques of reducing thickening of dentifrice may not be fully satisfactory since compared with a dentifrice filled into a flexible tube, when a dispenser is used the dentifrice must be relatively thin during filling but regains its consistency and remains so during the periods of shipping, storage and use. In other words, the dentifrice after filling essentially regains the consistency it had prior to the liquifying effect during shear filling for shipping, storage and use. Conventional gelling agents such as sodium carboxymethyl cellulose, hydroxyethyl cellulose or mixtures thereof may be desirably used for dentifrice containing alpha-alumina trihydrate polishing agent which is to be filled into a dispenser. However, when such a dentifrice contains many sources of active ingredients, such as at least two sources of fluorine, a desensitising agent such as allantoin ($C_7H_6N_4O_3$) and a vasodilator agent such as pyridyl carbinol,

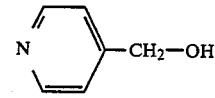

difficulties occur when the dentifrice is filled into a mechanically operated or pressure differential dispenser. In particular, dentifrice may seep through the space between a rod and a piston which are used particularly in a mechanically operated dispenser and leakage occurs at dispenser orifices. Further, the dentifrice ribbon extruded from a mechanically operated or pressure differential dispenser may be irregular or non-continuous. Since it is particularly desirable to prepare a dentifrice containing alpha-alumina trihydrate polishing agent which includes several active agents, such as those indicated above, due to compatability of such materials with the polishing agent, an alternative gelling system was needed.

Unexpectedly from amongst alternative types of gelling agents a mixture of a cellulosic gelling agent and i-carrageenan provides an excellent dentifrice containing alpha-alumina trihydrate and several active ingredients which is to be filled into and extruded from a mechanical or pressure differential dispenser. It has not been worthy that xanthan is not compatible with cellulosic gelling agents since it may contain cellulase.

It is an advantage of this invention that a dentifrice is provided which is readily filled into and extrudable from a mechanically operated or pressure differential dentifrice dispenser.

Other advantages will be apparent from consideration of the following specification.

In accordance with certain of its aspects, this invention relates to a dentifrice in a mechanically operated or pressure differential dispenser comprising about 20-80% by weight of an aqueous humectant vehicle, about 0.1-5% by weight of gelling agent mixture, about 20-75% by weight of alpha-alumina trihydrate polishing agent, sodium fluoride and sodium monofluorophosphate in amount to provide about 300 to 10000 ppm of fluorine, about 0.05–0.5% by weight of allantoin desensitising agent and about 0.05–0.5% by weight of pyridyl carbinol vasodilator agent, wherein said gelling agent mixture is a mixture of a cellulosic gelling agent and i-carrageenan in a weight ratio of cellulosic gelling agent to i-carrageenan of about 5:1 to about 1:5.

In the dentifrice formulation the dental vehicle comprises a liquid phase proportioned with the gelling agent to form an extrudable creamy mass of desirable consistency. The liquid phase in the dentifrice will comprise chiefly water and humectant such as polyols including glycerine, sorbitol, maltitol, xylitol, low molecular weight polyethylene glycol (e.g. 400 or 600), propylene glycol or the like including suitable mixtures thereof. It is advantageous usually to use as the liquid phase water and a humectant such as glycerine, sorbitol or polyethylene glycol, typically in amounts of about 10–55% by weight of water and about 20–50% by weight of humectant.

The dentifrice contains alpha-alumina trihydrate polishing agent in amounts of about 20–75% by weight. Alpha-alumina trihydrate is typically prepared by the Bayer process and used as particles below about 40 microns, principally about 3–20 microns, in size. Other polishing agents may be included such as insoluble sodium metaphosphate, dicalcium phosphate, calcined alumina, silica or calcium carbonate in minor amount with respect to alpha-alumina trihydrate.

The gelling agent mixture of the present invention is present in the dentifrice amount of about 0.1–5% by weight. It contains a cellulosic gelling agent mixed with i-carrageenan wherein the weight ratio of said cellulosic gelling agent to said i-carrageenan is from about 5:1 to about 1:5, preferably from about 1:1 to about 1:3, and the total gelling agent mixture is preferably about 0.2–3% by weight.

As mentioned above, iota carrageenan is commercially available as Genuvisco type 0819 and Viscarin TP-5 and has been recommended for use in a toothpaste. Such use in a toothpaste was described in Japanese Patent Publication No. 56 115711 of Lion Dentifrice Ltd, wherein i-carrageenan is mentioned as a possible component of a gelling system together with k-carrageenan and alkali metal alginate. In U.S. Pat. No. 4,353,890 to Scott, i-carrageenan is disclosed as an alternative to k-carrageenan as a toothpaste gelling agent wherein the toothpaste is subjected to microwave radiation to reduce the tendency of carrageenan in general to become thin during manufacture. The carrageenan may be sole gelling agent or mixed with other gelling agents. In the present invention, dentifrice containing i-carrageenan to be filled in a mechanically operated or pressure differential dispenser does not require microwave radiation.

The prior art generally discussed above does not indicate that gelling systems of cellulose gelling agent and i-carrageenan can provide dentifrices containing alpha-alumina trihydrate polishing agent and many active ingredients with the properties necessary for efficient filling into mechanically operated or pressure differential dispenser and extrusion therefrom.

It is noteworthy that U.S. Pat. No. 4,029,760 to de Roeck et al discloses an oral composition in which i-carrageenin is set forth as an antigingivitis agent alternative to other carrageenins. Carrageenins are highly depolymerised derivatives of carrageenans. Carrageenans do not appear to provide an antigingivitis effect.

Dentifrices are commonly manufactured by a cold process, e.g. at about 25° C., or by a hot process, e.g. at about 60° C. I-carrageenan can be used in either cold process or hot process techniques.

Physical properties of Genuvisco type 0819 i-carrageenan are indicated below:

1  Viscosity of 0.30% solution of GENUVISCO type 0819 in lean solvent prepared using a hot process (60° C.):
   Viscosity = 110 ± 17 cP at 32 rpm.
   Viscosity = 70 ± 11 cP at 64 rpm.
   Viscosity = 45 ± 7 cP at 128 rpm.
   Measured on HAAKE Rotovisco RV3 at 25° C.
2  Viscosity of 0.30% solution of GENUVISCO type 0819 in lean solvent prepared using a cold process (25° C.):
   Viscosity = 450 ± 60 cP measured on Brookfield Viscometer LVT at 25° C.
   Viscosity = 85 ± 13 cP at 32 rpm.
   Viscosity = 55 ± 8 cP at 64 rpm.
   Viscosity = 37 ± 6 cP at 128 rpm.
   Measured on HAAKE Rotovisco RV3 at 25° C.
3  Particle size: Less than 1% gum on 0.075 mm test sieve (DIN 80, 200 US mesh).
4  Moisture content: Less than 12%.
5  pH: 8.5 ± 1.5 in 0.5% solution in distilled water at 25° C.
6  Colour: White to cream.

Viscarin TP-5 i-carrageenan has the following physical properties:

| Colour | light tan to tan |
|---|---|
| Particle size | more than 95.0% through a US Standard Sieve, 250 nm (Series #60). |
| Moisture | maximum 12.0% (Cenco Moisture Balance). |
| pH | 7.0 to 9.5, 1.5% solution, 30° C. |

Typical desirable cellulosic gelling agents include alkali metal carboxymethyl cellulose, methyl cellulose, hydroxymethyl cellulose and hydroxypropyl cellulose. Sodium carboxymethyl cellulose is preferred. The mixed gel system is present in amount of about 0.1–5% by weight of the dentifrice, and the weight ratio of cellulosic gelling agent to i-carrageenan is from about 5:1 to about 1:5, preferably about 1:1 to about 1:3 and most preferably about 1:1. Thus, a typical preferred dentifrice can contain about 0.9–1.2% total gelling agent including about 0.3–0.9% of each of cellulosic gelling agent and i-carrageenan, the weight ratio between the two being from about 1:1 to 1:3.

It is noteworthy that grades of sodium carboxymethyl cellulose which may be used include the following:

TABLE 1

| SUPPLIER | CMC GRADE | VISCOSITY |
|---|---|---|
| Hercules | 7MXF | 300–500 |
| Hercules | 7MFD | 300–500 |
| Hercules | 9M31F | 900–1200 |
| Hercules | 9M31XF | 900–1200 |
| Hercules | 12M31XF | 900–1200 |
| Hercules | 7MF | 300–500 |
| Hercules | 12M31PD | 900–1200 |
| Hercules | 7M8SXF | 200–800 |
| Wolff Walsrode | Walocel CRT 1000 PA 07 | 700–1200 |
| Nyma | Nymcel ZMF.33* | 50–80 |
| Enka | Akucell AC 1642* | 80–120 |
| Enka | Akucell AC 1632* | 60–120 |
| Cros | Cellogen HP-SA | 700–900 |

TABLE 1-continued

| SUPPLIER | CMC GRADE | VISCOSITY |
|---|---|---|
| Uddeholm | Cekol MVEP | 500–800 |
| Hoechst | Tylose CB 200** | 120–260 |

*1% solution (Brookfield; 25° C.)
**Hoeppler Viscometer (2%; 20° C.).

Further, grades of hydroxyethyl cellulose which may be used include the following:

TABLE 2

| SUPPLIER | HEC GRADE | VISCOSITY |
|---|---|---|
| Hercules | Natrosol 250M and MR | 4500–6500 |
| Hercules | Natrosol 250 HR* and 250 H* | 1500–2500 |
| Hercules | Natrosol 250 HHR* and 250 HH | 3400–5000 |
| BP Chemicals | Cellobond 5000 A | 4200–5600 |
| BP Chemicals | Cellobond 7000 A | 6000–7000 |
| Hoechst | Tylose M 4000 P** | 3000–5000 |
| Hoechst | Tylose H 10000 P** | 7000–12000 |

*1% solution (Brookfield; 25° C.).
**Hoeppler Viscometer (2%; 25° C.).

The i-carrageenan and cellulosic gelling agent may be mechanically mixed together prior to mixing with the liquid phase of the dental cream vehicle or may be mixed separately with the liquid phase, with hot processing (typically about 60° C.) or cold processing (typically about 25° C.) techniques.

The dentifrice is packaged in a container from which it can be readily extruded such as a pressure differential or mechanically operated dental cream dispenser. The rheological properties are highly desirable when a mechanically operated dispensing container of the type described in British Patent Application No. 2,070,695A, published Sept. 9, 1981, is employed. This dispensing container comprises a dispensing mouthpiece, a tension member, a central rod, a piston and operating hand control. The disclosure of this published application is incorporated herein by reference.

Pressure differential dispensing container may be of the aerosol or vacuum type. Suitable pressure differential dispensers include those comprising a collapsible product-containing bag being disposed within a rigid container which contains a propellant fluid. In such dispensing containers, operation of the valve permits release of the product only, the propellant fluid being separated from the product by the fluid impermeable bag. Dispensers of this type are described in U.S. Pat. Nos. 3,828,977 and 3,838,796. These are the so-called Sepro dispensers. So-called Exxel containers also utilise pressure.

Still another type dispenser is the barrier piston container described in U.S. Pat. No. 4,171,757. Such container includes a valve, a product-containing compartment and an essentially fluid-tight barrier piston which separates the propellant fluid from the contained product (the so-called Diamond container).

The dentifrice contains as active agents a mixture of sodium fluoride and sodium monofluorophosphate to provide about 300–10000 ppm of fluorine, e.g. about 750–2000 ppm, and particularly about 1400–2000 ppm such as about 1400–1670 ppm. A binary fluoride system of sodium monofluorophosphate and sodium fluoride is desirably used in which about 30–40% of the fluorine (e.g. about 30–35%) is provided by sodium fluoride.

Sodium monofluorophosphate, $Na_2PO_3F$, as commercially available, may vary considerably in purity. It may be used in any suitable purity provided that any impurities do not substantially adversely affect the desired properties. In general, the purity is desirably at least 80%. For best results, it should be at least 85%, and preferably at least 90% by weight of sodium monofluorophosphate with the balance being primarily impurities or by-products of manufacture such as sodium fluoride and water-soluble sodium phosphate salt. Expressed in another way, the sodium monofluorophosphate employed should have a total fluoride content of above 12%, preferably above 12.7%, a content of not more than 1.5%, preferably not more than 1.2% of free sodium fluoride; preferably at least 12.1% all calculated as fluoride.

As indicated above, sodium fluoride in the binary mixture is a separate fluorine-containing component from sodium monofluorophosphate. About 225–800 ppm of fluorine is preferably provided to the dental cream by sodium fluoride.

Additional active agent is provided to the dentifrice by the presence of about 0.05–0.5% by weight, preferably about 0.08–0.2%, of allantoin desensitising agent. Such agent combats sensitivity of wounded periodontal tissue and promotes its healing. Allantoin can be obtained from ABM Industrial Products Ltd of Woodley, Stockport, Cheshire, England.

Pyridyl Carbinol active agent in amount of about 0.05–0.5% by weight, preferably about 0.08–0.2%, provides the dentifrice with a vasodilator effect.

When a dentifrice containing alpha-alumina trihydrate polishing agent, the binary fluoride system, allantoin desensitising agent and pyridyl carbinol vasodilator agent, described above, is employed filling and extrusion using mechanically operated or pressure differential dispensers is made efficient and rheologically desirable with the gel system of the invention.

Filling is effected by conventional techniques. For instance, when a mechanically operated dispenser of the type described in published British Patent Application No. 2,070,695A is used a predetermined amount of the dentifrice is extruded through a nozzle to fill the dispenser which is open at its bottom and which contains a central rod. A piston having a diameter corresponding to the inner diameter of the dispenser and a central hole to permit insertion of the central rod therein is slid into place. The dispenser is then sealed with a bottom disc.

Any suitable surface active or detersive material may be included in the dentifrice compositions. Such compatible materials are desirable to provide additional detersive, foaming aand anti-bacterial properties depending upon the specific type of surface active material and are selected similarly. These detergents are water-soluble compounds usually, and may be anionic, nonionic or cationic in structure. It is usually preferred to use the water-soluble non-soap or synthetic organic detergents. Suitable detersive materials are known and include, for example, the water-soluble salts of higher fatty acid monoglyceride monosulphate detergent (e.g. sodium coconut fatty acid monoglyceride monosulphate), higher alkyl sulphate (e.g. sodium lauryl sulphate), alkyl aryl sulphonate (e.g. sodium dodecyl benzene sulphonate, higher fatty acid esters of 1,2 dihydroxy propane sulphonate) and the like.

Further surface active agents include the substantially saturated higher aliphatic acyl amides of lower aliphatic amino carboxylic acid compounds, such as those having 12 to 16 carbons in the acyl radical. The amino acid portion is derived generally from the lower aliphatic saturated monoaminocarboxylic acids having about 2 to 6 carbons, usually the monocarboxylic acid compounds. Suitable compounds are the fatty acid amides of glycerine, sarconsine, alanine, 3-aminopropanoic acid and valine having about 12 to 16 carbons in the acyl group. It is preferred to use the N-lauroyl, myristoyl and palmitoyl sarcoside compounds, however, for optimum effects.

The amide compounds may be employed in the form of the free acid or preferably as the water-soluble salts thereof, such as the alkali metal, ammonium, amine and alkylolamine salts. Specific examples thereof are the sodium and potassium N-lauroyl, myristoyl and palmitoyl sacrosides, ammonium and ethanolamine N-lauroyl glycide and alanine. For convenience herein, reference to "amino carboxylic acid compound", "sarcoside", and the like refers to such compounds have a free carboxylic group of the water-soluble carboxylate salts.

Such materials are utilised in pure or substantially pure form. They should be as free as practicable from soap or similar higher fatty acid material which tends to reduce the activity of these compounds. In usual practice, the amount of such higher fatty acid materials is less than 15% by weight of the amide and insufficient to substantially adversely affect it, and preferably less than about 10% of said amide material.

Various other materials may be incorporated in the dentifrice of this invention. Examples thereof are colouring or whitening agents, preservatives, such as methyl p-hydroxybenzoate, stabilisers, tetrasodium pyrophosphate, silicones, chlorophyll compounds and ammoniated materials such as urea, diammonium phosphate and mixtures thereof. These adjuvants are incorporated in the instant compositions in amount which do not substantially adversely affect the desired properties and characteristics and are suitably selected and used in conventional amounts.

For some purposes it may be desirable to include antibacterial agents in the compositions of the present invention. Typical antibacterial agents which may be used in amounts of about 0.01% to about 5%, preferably about 0.05% to about 1.0%, by weight of the dentifrice composition include:

$N^1$-4(chlorobenzyl-$N^5$-(2,4-dichlorobenzyl)biguanide;
p-chlorophenylbiguanide;
4-chlorobenzhydrylbiguanide;
4-chlorobenzhydrylguanylurea;
N-3-lauroxypropyl-$N^5$-p-chloroenzylbiguanide;
1,6-di-p-chlorobenzylbiguande;
1-(lauryldimethylammonium)-8-(p-chlorobenzyl-dimethyl-ammonium)octane dichloride;
5,6-dichloro-2-guanidinobenzimidazole;
$N^1$-p-chlorophenyl-$N^5$-laurylbiguanide;
5-amino-1,3-bis(2-ethylhexyl)-5-methylhexahydropyrimidine;
and their non-toxic acid addition salts.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange as well as methylsalicylate. Suitable sweetening agents include sucrose, lactose, maltose, sorbitol, sodium cyclamate, sodium saccharine dipeptides of U.S. Pat. No. 3,939,261 and oxathiazin salts of U.S. Pat. No. 3,932,606. Suitable flavour and sweetening agent may together comprise from about 0.01 to 5% or more of the composition.

The dentifrices should have a pH practicable for use. A pH range of 3 to 10.5 is particularly desirable. The reference to the pH is meant to be the pH determination directly on the dentifrice. If desired, materials such as benzoic or citric acid may be added to adjust the pH to, say 4 to 8.5.

The following examples are further illustrative of the nature of the present invention, but it is to be understood that the invention is not limited thereto. All amounts of the various ingredients are by weight unless otherwise specified.

EXAMPLE 1

The following dentifrice is prepared by conventional room temperature cold process and filled into the mechanically operated dispenser described in British Patent Publication No. 2,070,695A.

|  | Parts |
| --- | --- |
| Sorbitol (70%) | 23.000 |
| Sodium Saccharin | 0.170 |
| I-carrageenan (Genuvisco 0819) | 0.500 |
| Sodium Carboxymethyl cellulose (7MFD) | 0.500 |
| Methyl p-hydroxybenzoate | 0.080 |
| Allantoin | 0.150 |
| Sodium Fluoride | 0.100 |
| Sodium Monofluorophosphate | 0.760 |
| Pyridyl Carbinol | 0.100 |
| Alpha alumina trihydrate (Alcoa C-333) | 51.000 |
| Benzoic Acid | 0.140 |
| Sodium Lauryl Sulphate | 1.667 |
| Titanium Dioxide | 0.500 |
| Flavour | 1.200 |
| Deionised water | 20.133 |

The dentifrice fills efficiently into the dispenser and does not undergo leakage during storage at 43° C. for over 1 month. It extrudes well from the dispenser after 1 month storage at 43° C.

Similar satisfactory results are attained when the dentifrice is modified to contain 0.55 parts of each of i-carrageenan and sodium carboxymethyl cellulose in one case and 0.45 parts of each of i-carrageenan and sodium carboxymethyl cellulose in a second case, with corresponding adjustment of the water contents. Indeed absence of leakage and good extrudibility after storage at 43° C. for 3 months are observed with these dentifrices.

Again satisfactory results are observed when each of the three dentifrices described above are modified to contain 50.000 parts of alpha-alumina trihydrate in one set of these dentifrices and 52.000 parts of alpha-alumina trihydrate in the second set of three dentifrices, with corresponding adjustment of the water contents.

EXAMPLE 2

The following dentifrice is prepared by cold process and filled into the same dispenser as in Example 1.

|  | Parts |
| --- | --- |
| Sorbitol (70%) | 23.000 |
| Sodium Saccharin | 0.170 |
| I-carrageenan (Genuvisco 0819) | 0.666 |
| Sodium carboxymethyl cellulose (7MFD) | 0.334 |
| Methyl p-hydroxybenzoate | 0.080 |
| Allantoin | 0.150 |
| Sodium Fluoride | 0.100 |
| Sodium Monofluorophosphate | 0.760 |

-continued

| | Parts |
|---|---|
| Pyridyl carbinol | 0.100 |
| Alpha alumina trihydrate (Alcoa C-333) | 51.500 |
| Benzoic Acid | 0.140 |
| Sodium lauryl sulphate | 1.667 |
| Titanium Dioxide | 0.500 |
| Flavour | 1.200 |
| Deionised water | 19.633 |

The dentifrice fills efficiently into the dispenser and does not undergo leakage and extrudes well from the dispenser after storage for 1 month at 43° C.

Similar desirable effects are attained when the dentifrices of the examples are filled into a pressure differential dispenser.

When sodium carboxymethyl cellulose is used as the only gelling agent poor extrusion occurs. When hydroxyethyl cellulose is used as the only gelling agent leakage occurs. However, when hydroxyethyl cellulose is mixed with i-carrageenan desirable filling and extrusion is attained.

It will be apparent to those skilled in the art that further modifications of the examples illustrative of the invention, may be made thereto.

We claim:

1. A dentifrice suitable for use in a mechanically operated or pressure differential dispenser comprising about 20–80% by weight of an aqueous humectant vehicle, about 0.1–5% by weight of gelling agent mixture, about 20–75% by weight of alpha-alumina trihydrate polishing agent, sodium fluoride and sodium monofluorophosphate in amount to provide about 300 to 10000 ppm of fluorine, about 0.05–0.5% by weight of allantoin desensitising agent and about 0.05–0.5% by weight of pyridyl carbinol vasodilator agent, wherein said gelling agent mixture is a mixture of a cellulosic gelling agent and i-carrageenan in a weight ratio of cellulosic gelling agent to i-carrageenan of about 5:1 to about 1:5.

2. The dentifrice claimed in claim 1 wherein the weight ratio of said cellulosic gelling agent to said i-carrageenan is about 3:1 to about 1:3 and the gelling agent mixture is present in amount of about 0.2–3% by weight.

3. The dentifrice claimed in claim 2 wherein said cellulosic gelling agent is sodium carboxymethyl cellulose.

4. The dentifrice claimed in claim 2 wherein the weight ratio of said cellulosic gelling agent to said i-carrageenan is about 1:1.

5. The dentifrice claimed in claim 1 wherein said sodium fluoride and said sodium monofluorophosphate are present in amount to provide about 750–2000 ppm of fluorine and about 30–40% of the fluorine is provided by said sodium fluoride.

* * * * *